United States Patent
Tuohy et al.

(10) Patent No.: US 10,369,326 B2
(45) Date of Patent: Aug. 6, 2019

(54) CATHETER WITH A LUMEN SHAPED AS AN IDENTIFICATION SYMBOL

(71) Applicant: Medtronic Vascular, Inc., Santa Rosa, CA (US)

(72) Inventors: John Tuohy, Clare (IE); Sean Ward, Dublin (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 16 days.

(21) Appl. No.: 15/372,792

(22) Filed: Dec. 8, 2016

(65) Prior Publication Data

US 2017/0165454 A1 Jun. 15, 2017

Related U.S. Application Data

(60) Provisional application No. 62/265,237, filed on Dec. 9, 2015.

(51) Int. Cl.
| | |
|---|---|
| *A61M 25/00* | (2006.01) |
| *A61M 25/01* | (2006.01) |
| *A61M 31/00* | (2006.01) |
| *A61B 90/00* | (2016.01) |
| *A61B 90/96* | (2016.01) |
| *B29C 59/16* | (2006.01) |
| *B29L 31/00* | (2006.01) |

(52) U.S. Cl.
CPC ......... *A61M 25/0023* (2013.01); *A61B 90/39* (2016.02); *A61B 90/96* (2016.02); *A61M 25/0108* (2013.01); *A61M 31/005* (2013.01); *A61B 2090/3933* (2016.02); *A61B 2090/3966* (2016.02); *A61M 25/0009* (2013.01); *A61M 2205/32* (2013.01); *A61M 2205/6072* (2013.01); *A61M 2207/00* (2013.01); *B29C 59/16* (2013.01); *B29L 2031/7543* (2013.01)

(58) Field of Classification Search
CPC ............ A61M 25/0023; A61M 31/005; A61M 2207/00; A61M 25/0012; A61M 25/0028; A61M 25/0029; A61M 25/0032; A61M 2025/0034; A61M 25/0108; A61B 90/96
See application file for complete search history.

(56) References Cited

U.S. PATENT DOCUMENTS

| | | | | |
|---|---|---|---|---|
| 5,320,100 A | * | 6/1994 | Herweck | A61F 2/06 128/899 |
| 2007/0004981 A1 | | 1/2007 | Boese et al. | |

(Continued)

OTHER PUBLICATIONS

PCT/US2016/065655, The International Search Report and the Written Opinion of the International Searching Authority, dated Mar. 23, 2017, 19pgs.

*Primary Examiner* — Theodore J Stigell
(74) *Attorney, Agent, or Firm* — Medler Ferro Woodhouse & Mills PLLC

(57) ABSTRACT

A catheter includes a catheter shaft having a shaft wall and a lumen extending longitudinally within the shaft wall. The lumen is bounded in radially outward and radially inward directions. The lumen includes a feed portion and an identification symbol fluidly connected to the feed portion. The lumen is configured to receive a contrast media. The lumen may be formed by a channel formed in an outer surface of a first shaft of the catheter shaft, and a covering disposed around the outer surface of the first shaft to cover the channel.

12 Claims, 8 Drawing Sheets

(56) References Cited

U.S. PATENT DOCUMENTS

| | | | |
|---|---|---|---|
| 2007/0088323 A1* | 4/2007 | Campbell | A61M 25/10 604/523 |
| 2008/0125754 A1 | 5/2008 | Beer et al. | |
| 2015/0217085 A1 | 8/2015 | Haverkost et al. | |

* cited by examiner

CATHETER WITH A LUMEN SHAPED AS AN IDENTIFICATION SYMBOL

CROSS-REFERENCE TO RELATED APPLICATIONS

This application claims the benefit under 35 U.S.C. § 119(e) of the filing date of U.S. Provisional Application No. 62/265,237 filed Dec. 9, 2015, the contents of which are incorporated by reference herein in their entirety.

FIELD OF THE INVENTION

The present disclosure relates to a catheter including a lumen with a portion shaped as an identification symbol configured to receive a contrast media for visualization under fluoroscopy.

BACKGROUND OF THE INVENTION

Catheters are thin tubes utilized for insertion into the vessels of a body to perform a variety of medical procedures, including draining fluids, administering fluids, measuring internal body pressures, angioplasty procedures, delivery and deployment of stents or other prostheses (e.g. heart valve prostheses), and other such procedures. The catheters are often made of highly flexible material, capable of following the path of an artery or vein until the target area is reached and the medical procedure is begun. It is, however, difficult to know the exact location of a catheter within use in the body during a medical procedure.

In some procedures, to achieve proper placement within the vessel, a physician must know the exact location of the distal end of the catheter within in the body. Fluoroscopy can be used to determine the location of a catheter within the body. Fluoroscopy is an imaging technique that utilizes a stream of X-rays to generate a series of images of the internal features of a body on a screen. The images are continuously updated in a way that resembles a real-time video. However, catheters are often made from materials that are not easily seen via fluoroscopy. Therefore, radiopaque marker bands are often added to catheters at critical locations, such as a distal end of the catheter or the location of a stent within the catheter. In another example, radiopaque material may embedded within the polymers of the catheter. In yet another example, radiopaque ink may be applied to an exterior surface of the catheter.

In many procedures, multiple catheters and other devices may be simultaneously present in the body of the patient. Therefore, while radiopaque markers enable a treating clinician to view a particular area of a catheter, the clinician may not be able to distinguish one particular catheter from other catheters or devices in the body. Additionally, information such as the catheter brand, size of a balloon or stent, batch number, etc. are of importance to prevent or eliminate the chances that one catheter or medical tool is mistaken for another.

Accordingly, there exists a need for a catheter with an identifier that can be seen under fluoroscopy and can provide certain information regarding the catheter.

BRIEF SUMMARY OF THE INVENTION

Embodiments hereof are directed to a catheter including a catheter shaft having a shaft wall and a lumen extending longitudinally within the shaft wall. The lumen is bounded in radially outward and radially inward directions. The lumen includes a feed portion and an identification symbol fluidly connected to the feed portion. The lumen is configured to receive a contrast media. In some embodiments, the lumen is formed by a channel formed in an outer surface of a first shaft of the catheter shaft, and a covering disposed around the outer surface of the first shaft to cover the channel.

Embodiments hereof are also directed to a method of forming an identification symbol on a catheter for viewing under fluoroscopy. The method includes ablating a channel into an outer surface of a catheter shaft. The channel includes a feed portion and an identification symbol having a pattern, the feed portion and the identification symbol being fluidly connected. The method further includes covering the feed portion and the identification symbol of the channel to form an enclosed lumen including the feed portion and the identification symbol, wherein the lumen is configured to be filled with a contrast media.

Embodiments hereof are also directed to a method of identifying a catheter within a body of a patient. The method includes inserting a catheter into a body of a patient. The catheter includes a catheter shaft having a lumen formed in a wall of the catheter shaft, the lumen including a feed portion and an identification symbol in fluid communication with the feed portion. The method further includes injecting a contrast media into the lumen such that the contrast media reaches the identification symbol. The method further includes viewing the identification symbol under fluoroscopy.

BRIEF DESCRIPTION OF DRAWINGS

The foregoing and other features and advantages of the invention will be apparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, where like reference numbers indicate identical or functionally similar elements. The terms "distal" and "proximal", when used in the following description to refer to a catheter or delivery system are with respect to a position or direction relative to the treating clinician. Thus, "distal" and "distally" refer to positions distant from, or in a direction away from the treating clinician, and the terms "proximal" and "proximally" refer to positions near, or in a direction toward the clinician.

Figure 1:
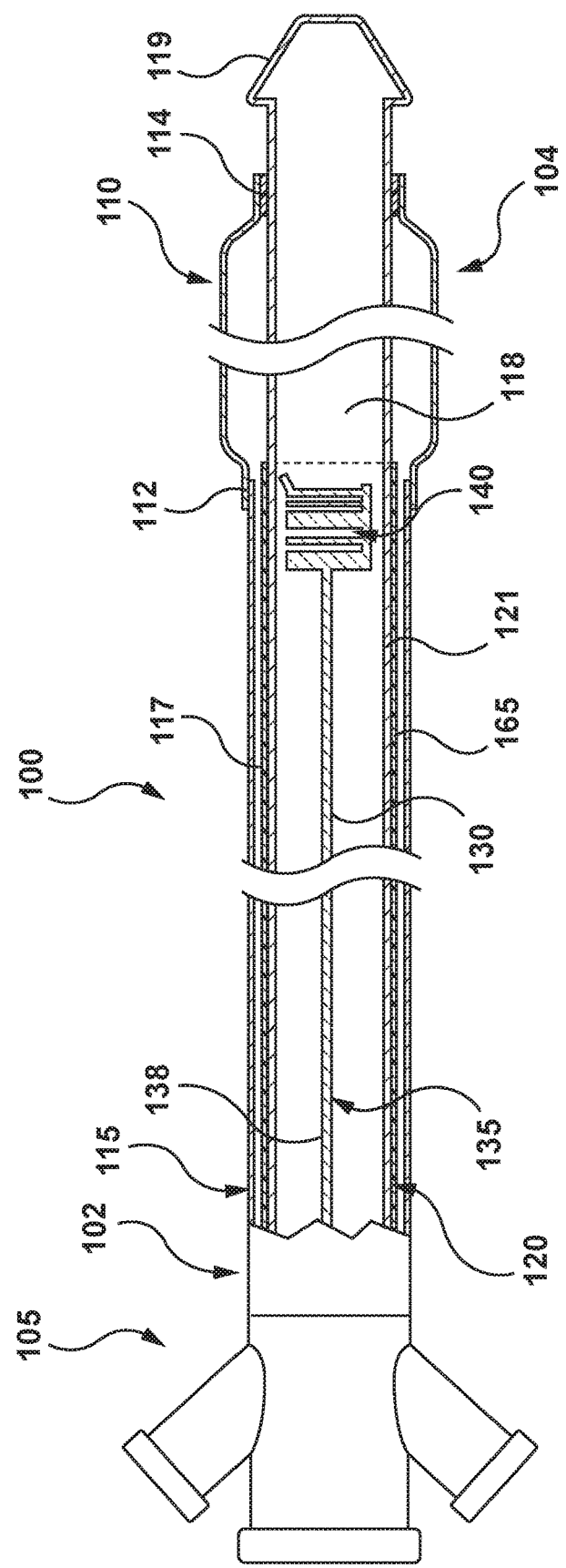
FIG. 1 is a schematic illustration of an exemplary catheter in accordance with an embodiment thereof.

An exemplary catheter 100 in accordance with an embodiment hereof is shown in FIG. 1. The catheter 100 is configured for viewing during fluoroscopy by incorporating a contrast media-holding lumen along the length of the catheter. A contrast media can be injected into the lumen for viewing using fluoroscopy.

Referring to FIG. 1, the exemplary catheter 100 is a balloon catheter. However, this is merely an example and other types of catheters may incorporate the features disclosed herein. In the embodiment shown, the catheter 100 includes an outer shaft 115, an inner shaft 120 disposed within a lumen of the outer shaft 115, and an inflatable member or balloon 110. The catheter 100 includes a proximal portion 102 that extends out of the body and includes a hub or luer 105. The balloon 110 is disposed at a distal portion 104 of the catheter 100. In the embodiment shown, a proximal portion of the balloon 110 is coupled to a distal portion of the outer shaft 115 at a proximal bond 112 and a distal portion of the balloon 110 is coupled to a distal portion of the inner shaft 120 at a distal bond 114. A distal tip 119 is also coupled to a distal portion of the inner shaft 120. The inner shaft defines a lumen 118 therein, generally used as a guidewire lumen. Further, an inflation lumen 117 is defined between an outer surface of the inner shaft 120 and an inner surface of the outer shaft 115. The inflation lumen 117 is in communication with an interior of the balloon 110, as shown in FIG. 1. The general features of the catheter 100 described above are not meant to be limiting and are provided for context of the drawings only. Other catheters with or without a balloon, or including only a single shaft rather than outer and inner shafts, may incorporate the features of the present disclosure.

In the embodiment shown, the inner shaft 120 includes a lumen 135 extending along the length of the inner shaft 120, from the proximal luer 105 to a distal portion of the inner shaft 120. The lumen 135 is formed longitudinally in a wall 126 (FIG. 2E) of the inner shaft 120. The termed "longitudinally" as used with respect to the lumen 135 formed in the wall of a shaft does not limit the lumen to a direction that is parallel to a central longitudinal axis of the shaft. Instead, the term means that the lumen 135 does not extend through the wall of the shaft radially (i.e. radially inward or outward). Thus the lumen in the shaft wall can vary circumferentially within the shaft wall to form patterns, as explained in more detail below. As shown in FIG. 1, a proximal or feed portion 138 of lumen 135 is an elongate feed lumen and a distal portion of the lumen 135 forms an identification symbol 140. The feed portion 138 of the lumen 135 is in fluid communication with the distal portion of the lumen 135 forming the identification symbol 140. The lumen 135 (including the identification symbol 140) is configured to receive contrast media 170 (see FIGS. 3-6) therein such that with the catheter 100 in a vessel of the patient, the identification symbol 140 can be seen under fluoroscopy. The contrast media 170 may be any contrast media, such as but not limited to iodine based contrast media.

FIG. 1 is a schematic figure to show the lumen 135. As explained in more detail below, the lumen 135, including the identification symbol 140, is formed as a channel 130 in a first shaft 121 with a film covering 165 covering the first shaft 121 to close the lumen 135. Thus, as described herein, the lumen 135 is a closed lumen such that the contrast media does not escape the lumen 135.

The identification symbol 140 shown in FIG. 1 functions as a bar code for recognizing the catheter 100 using fluoroscopy during a procedure. In the embodiment shown in FIG. 1, the identification symbol 140 is a barcode with a series of parallel lines having varied widths. However, other types of identification symbols, described below or others, may also be utilized. The identification symbol 140 is a machine-readable symbol. Thus, software or other devices which can read the identification symbol 140 when displayed on a screen can be used to read the identification symbol 140. The identification symbol 140 can provide information regarding the catheter 100, such as, but not limited to, the manufacturer, patient information, type of catheter, the size of the balloon 110, size of a stent mounted on the balloon 110, size of a stent mounted within a sheath of a catheter, batch number, or other information that may be deemed useful.

Figure 2A:
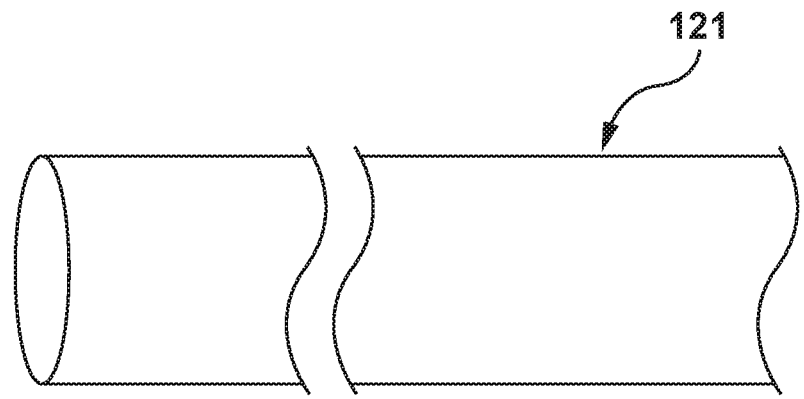
FIGS. 2A-2D are schematic illustrations of steps in forming a lumen in the wall of a shaft in accordance with an embodiment hereof.

The lumen 135 is an enclosed lumen disposed longitudinally through a wall of the inner shaft 120. The lumen 135 may be formed by a variety of methods. A preferred method of forming the lumen 135 in the inner shaft 120 is described with reference to FIGS. 2A-2E. In this method, the inner shaft 120 is formed of a shaft 121 and a film covering 165 disposed around an outer (first) surface 122 of the shaft 121. Thus, in a first step of the method, the shaft 121 is provided, as shown in FIG. 2A.

Figure 2B:
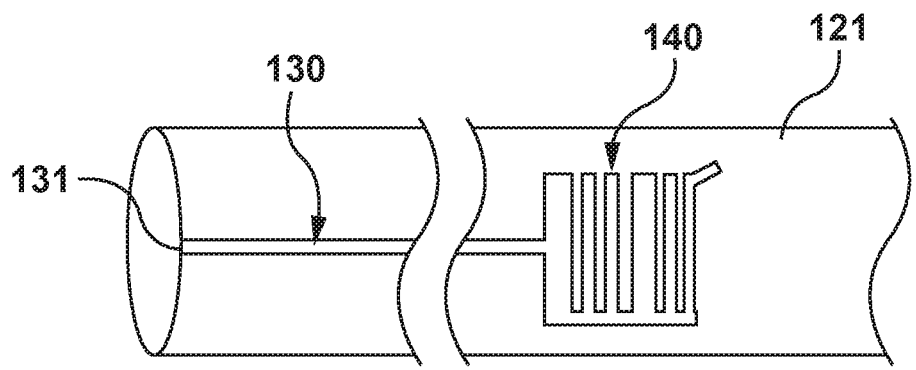

Referring to FIG. 2B, a channel 130 is formed into the outer surface 122 of the shaft 121. The channel 130 is in the shape of the lumen 135, including the identification symbol 140 at a distal portion of the channel 130. The channel 130 may be ablated into the outer surface 122 of the shaft 121 using a laser, such as a laser having an ultrashort pulse rate (i.e. femtosecond durations), capable of ablating a channel in a controlled manner at a depth of approximately 0.001-0.002" throughout the length of the channel 130. The identification symbol 140 is also formed as part of the channel 130, and may be formed at approximately the same depth of approximately 0.001-0.002". In another example, the channel 130 may be produced via a chemical etching/milling process to remove material from the shaft 121. In such a method, a mask is provided on areas of the shaft 121 that are not to be etched. Such a mask would leave an unmasked portion of the shaft 121 in the shape of the channel 130 and the identification symbol 140. The shaft 121 is then immersed or otherwise exposed to an etchant, such as a chemical, which causes the exposed portions of the shaft 121 to be dissolved in a controlled manner. The process is controlled by correlating the exposure time of the shaft 121 to the etchant with the intended etching depth. Etching enables the production of highly complex and accurate etched shapes within the desired depth between 0.001-0.002".

Figure 2C:
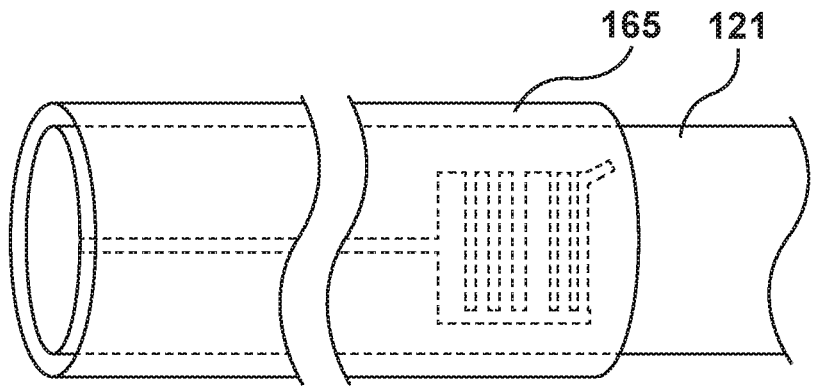
Figure 2D:
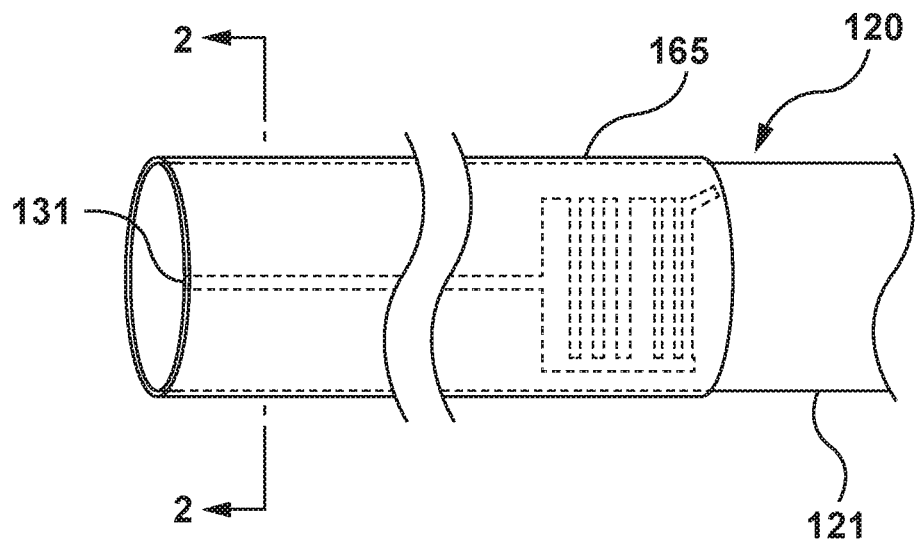

With the channel 130 including the identification symbol 140 formed into the outer surface 122 of the shaft 121, the film covering 165 is disposed over the shaft 121, as shown in FIG. 2C. The film covering 165 may be a heat shrink tube formed from a polymer, such as, but not limited to, polyurethane, fluorinated ethylene-propylene, tetrafluoroethylene and polyesters. As shown in FIG. 2C, film covering 165 is in the form of a tube that fits loosely over the shaft 121. Once heated, the film covering 165 shrinks to tightly fit against the outer surface 122 of shaft 121, thereby covering the channel 130 to form the lumen 135, as shown in FIG. 2D. As also shown in FIG. 2D, the lumen 135 includes a proximal opening 131 configured to receive the contrast media therein. The proximal opening 131 is fluidly coupled to a source of contrast media. However, other types of openings or sources to inject the contrast media into the lumen 135 may be utilized.

Figure 2E:
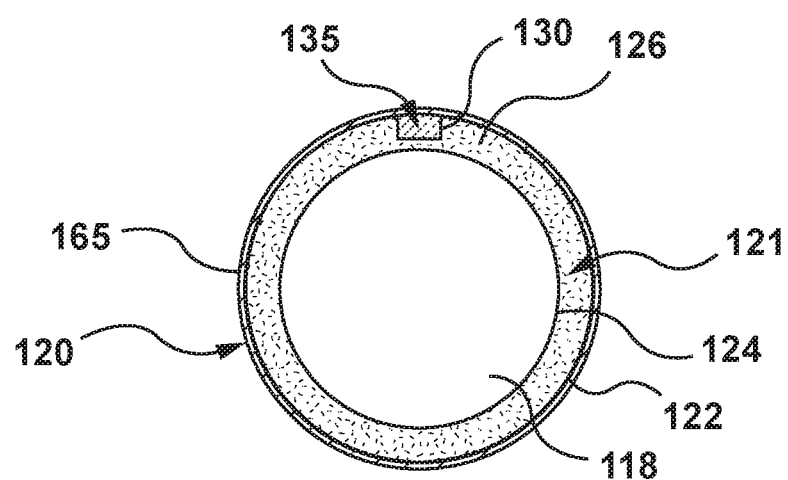
FIG. 2E is a cross-sectional illustration of the inner shaft of the catheter of FIG. 1 taken along line 2-2 of FIG. 2D.

FIG. 2E is a cross-sectional view taken along line 2-2 of the inner shaft 120 of shown in FIG. 2D. As explained above, the inner shaft 120 includes the shaft 121 and the film covering 165 disposed around the shaft 121. The shaft 121 includes the outer (first) surface 122 and an inner (second) surface 124, with the shaft wall 126 between the outer surface 122 and the inner surface 124. The outer 122 surface of the shaft 121 includes the ablated channel 130, as described above. The channel 130 has a depth less than a thickness of the wall 126, preferably between 0.001-0.002" in depth from the outer surface 122.

FIGS. 3-6 display schematic illustrations of various embodiments of the identification symbol 140 formed by the channel 130 forming the lumen 135. The illustrations of FIG. 3-6 are side views of a longitudinal portion of the inner shaft 120 with the polymeric covering 165 removed. Thus, in FIGS. 3-6, the channel is 130 uncovered. However, it is understood that the channel 130 is covered to form the lumen 135, whether by the film covering 165 of other methods.

Figure 3:
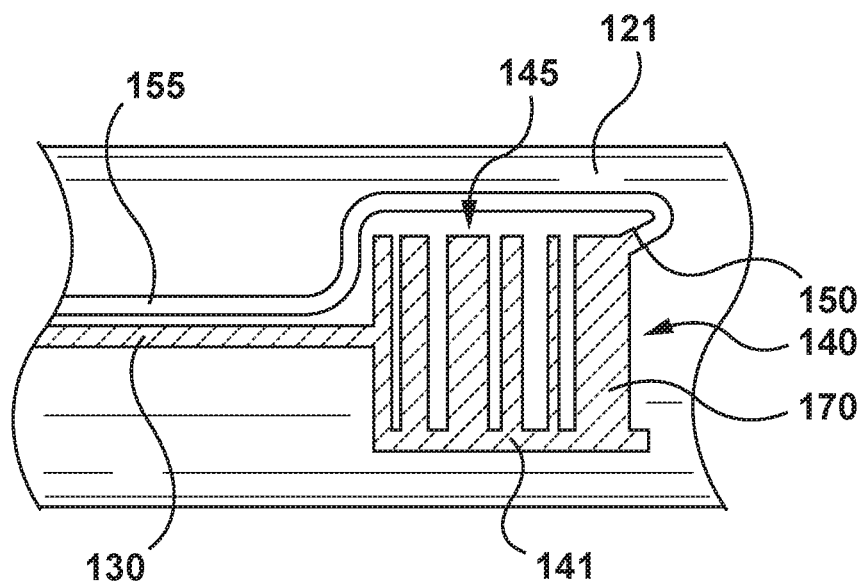
FIG. 3 is a schematic illustration of a channel and an identification symbol of a catheter in accordance with an embodiment hereof.

Referring to FIG. 3, as noted above with respect to FIG. 1, the ablation pattern forms the identification symbol 140 resembling a barcode, with a multitude of parallel lines 145 having varied widths. In the embodiment of FIG. 3, the parallel lines 145 of the identification symbol 140 are fluidly connected to one another via a communication channel 141 disposed at an end of the parallel lines 145. The identification symbol 140 is also fluidly connected to proximal portion 138 of the channel 130.

Figure 6:
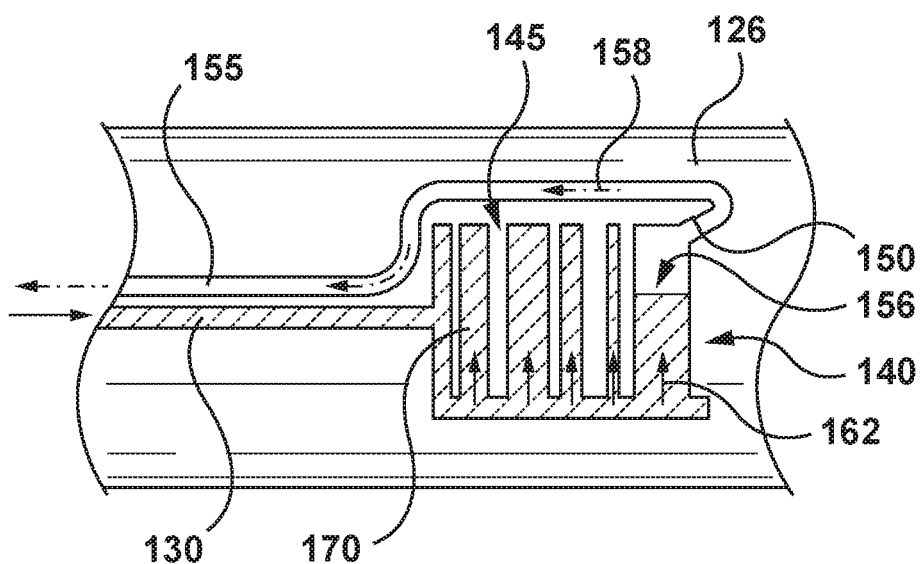
FIG. 6 is a schematic view of the identification symbol and fluid flow through the identification symbol.

As also shown in FIG. 3 and in more detail in FIG. 6, an air evacuation port 150 is provided at a distal end of the identification symbol 140. The air evacuation port 150 enables air to escape the lumen 135 as the contrast media 170 is injected into the lumen 135. As shown in FIG. 6, as the lumen 135 of the identification symbol is being filled, air in open space 156 is pushed through the air evacuation port 15. The air evacuation port 150 may be in communication with an air lumen 155 that extends from the air evacuation port 150 proximally back through the wall 126 of the inner shaft 120. The air is pushed back through the air lumen 155, as indicated by arrow 158, and may escape the air lumen 155 through an opening (not shown) at the proximal end of the inner shaft 120. In such an embodiment, a valve may be provided at the proximal end of the catheter 100 such that a clinician may control flow. In other embodiments, the air evacuation port 150 may extend through the film covering 165 to the inflation lumen 117 between the inner shaft 120 and the outer shaft 115. The air may then escape proximally through the inflation lumen 117 and the luer 105. In other embodiments, the air evacuation port 150 and the air lumen 155 may be eliminated. Air in the lumen 135 may instead be evacuated by pulling a vacuum from a proximal end of the lumen 135, such as through the proximal opening 131. Other air evacuation paths or methods may also be used, provided that the air is not evacuated into the patient.

Figure 4:
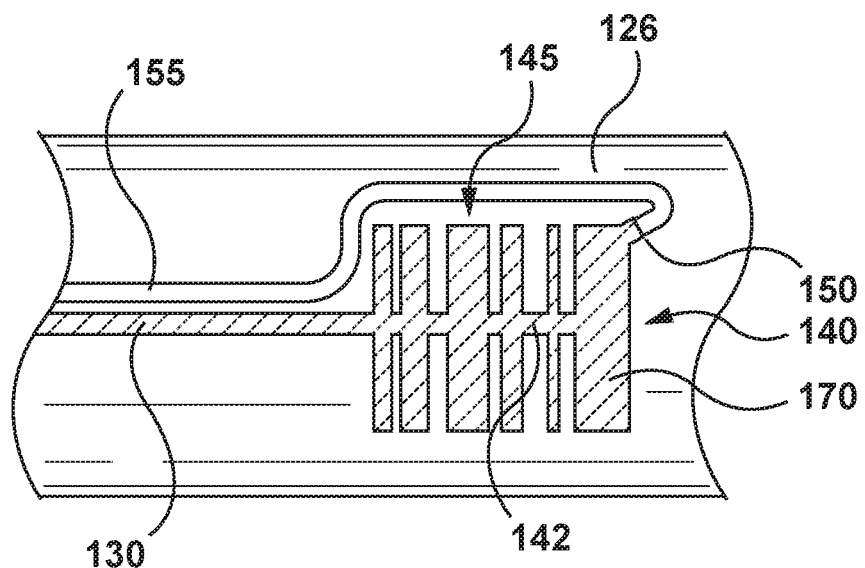
FIG. 4 is a schematic illustration of a channel and an identification symbol of the catheter in accordance with another embodiment hereof.

Referring now to FIG. 4, the parallel lines 145 of the identification symbol 140 may be the same as the embodiment of FIG. 3. However, instead of the communication channel 141 disposed at an end of the parallel lines 145, as in FIG. 3, a communication channel 142 is providing between the parallel lines 145. The communication channel 142 of FIG. 4 is disposed at approximately the midway point of the parallel lines 145 and is essentially an extension of the channel 130. FIGS. 3 and 4 show two different examples of how the feed portion 138 of the lumen 135 feeds the contrast media into the identification symbol 140. However, these are not meant to be limiting. The feed portion 138 may feed into different portions of the identification symbol 140 depending on where the distal end of the feed portion is located relative to the identification symbol 140, such as the "bottom" or "top" (or both (the feed portion can split) of the parallel lines 145 shown in FIGS. 3 and 4, recognizing that the terms "top" and "bottom" are used only for convenience of explaining locations in the figures. Further, the parallel lines 145 of the identification symbol may be filled serially or in parallel.

Figure 5:
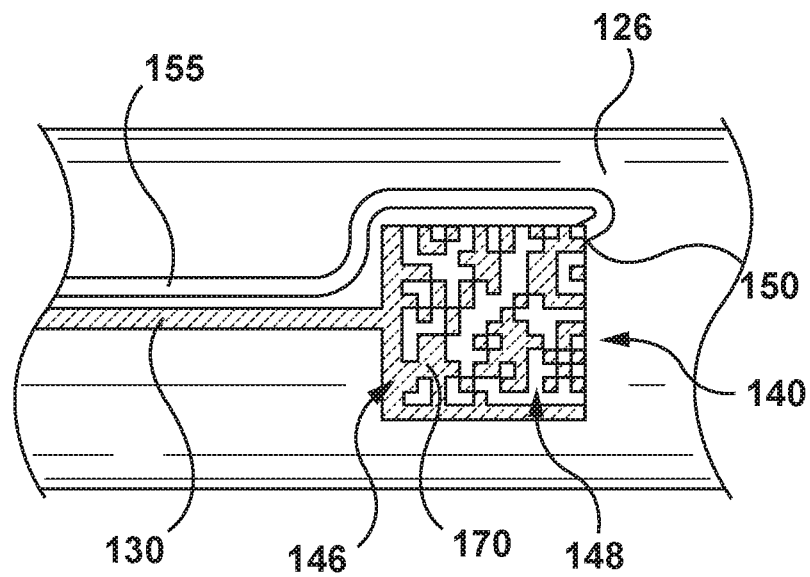
FIG. 5 is a schematic illustration of a channel and an identification symbol of the catheter in accordance with another embodiment hereof.

FIG. 5 displays another embodiment of the identification symbol 140. The identification symbol 140 of FIG. 5 resembles a matrix or two-dimensional barcode. The matrix barcode embodiment of the identification symbol 140 includes a plurality of light areas 148 and dark areas 146, formed by unablated segments and ablated segments in the shaft 121, respectively. Thus, in the method described above with respect to FIGS. 2A-2D, the dark areas 148 are formed by ablating (e.g., by laser or chemical etching) those segments of the shaft 121. Thus, when the contrast media 170 is injected through the lumen 135, the ablated segments are filled with the contrast media 170, thereby forming the dark areas 146, while the unablated segments do not include a lumen to be filled with the contrast media, thereby forming the light areas 148. With the identification symbol 140 filled with the contrast media 170, software or other devices which can read the identification symbol 140 when displayed on a screen can be used to read the identification symbol 140. In the illustrated embodiment, the identification symbol 140 (matrix barcode) is contained within a conventionally square-shaped perimeter, however, other bordering shapes are contemplated.

Figure 7:
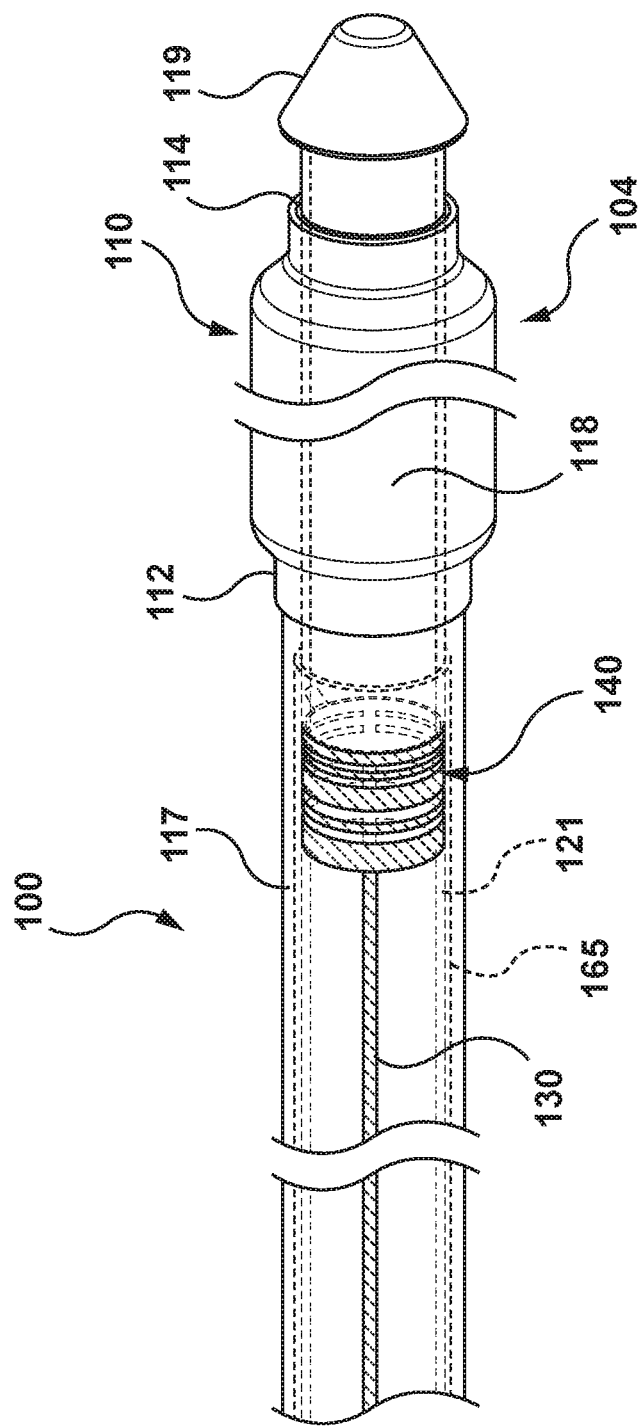
FIG. 7 is a schematic perspective view of an exemplary catheter with a spiral identification symbol.
Figure 8:
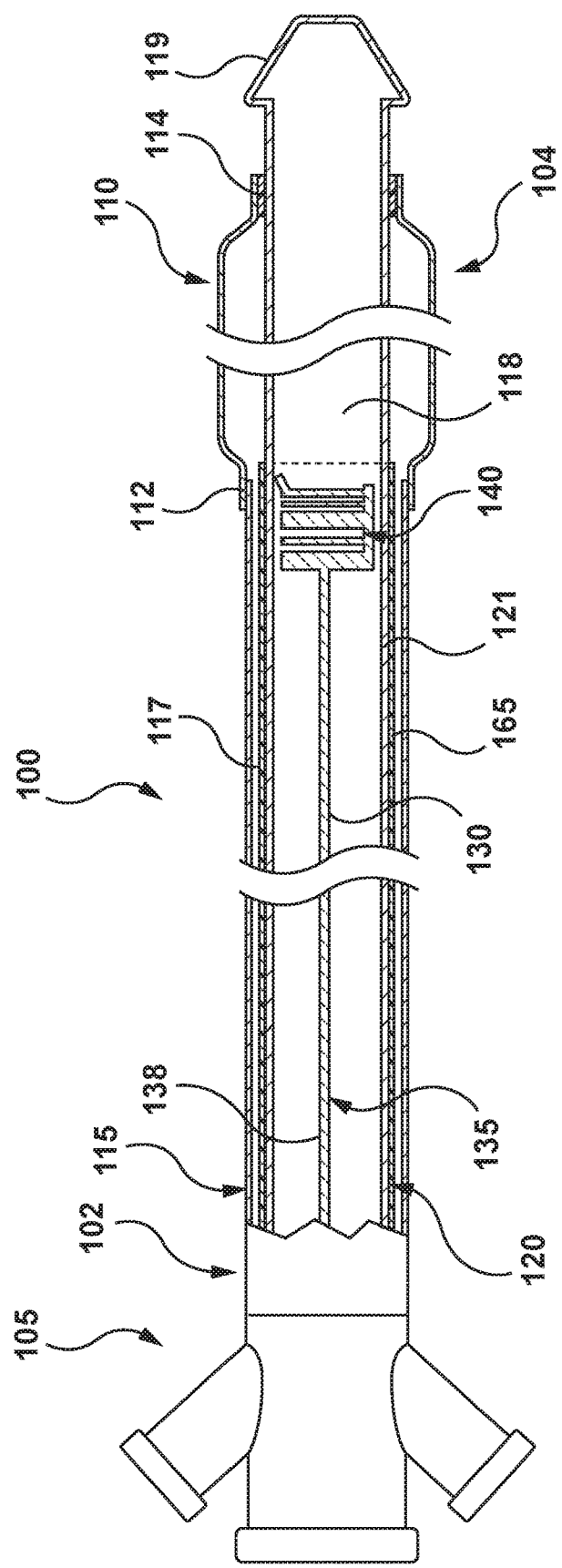
FIG. 8 is a side view of the catheter of FIG. 7.

In other embodiments, such as shown in FIGS. 7-8, the identification symbol 140 may be a spiral pattern 141 wrapped around the inner shaft 120. The spiral pattern 141 is formed by forming a lumen in the wall of the inner shaft 120. The width of the lumen and separation between bands of the lumen may be varied to create the identification symbol 140. As discussed above, the lumen may be formed by ablating a channel into the wall of the shaft 121 and then heat shrinking the polymer film covering 165 over the shaft 121. Varying the width of the channel and the separation between adjacent bands of the channel forms the identification symbol 140. When filled with the contrast media 170, the lumen is visible via fluoroscopy. When viewed on a two-dimensional fluoroscopic screen, the spiral pattern 141 is viewed as a conventional barcode, as shown in FIG. 8. The spiral pattern identification symbol enables the identification symbol to be properly viewed when the identification symbol is oriented in a variety of positions within the body, thereby preventing the blocking of the identification symbol from fluoroscopic viewing when the symbol is not optimally oriented for viewing.

In a further non-limiting example, the identification symbol 140 may also provide information regarding the rotational orientation of the catheter 100. For example, certain procedures, such as transcatheter valve replacement, may require that a device mounted on or within a catheter be rotationally oriented in a particular way before deployment of the device from the catheter. In an embodiment, the identification symbol 140 may be disposed on the catheter 100 such that the identification symbol 140 cannot be properly read unless the catheter 100 is in the proper rotational orientation. Thus, when identification symbol 140 is readable, the clinician knows the proper orientation has been achieved. As explained above, the identification symbol is read by computer software. If the identification symbol 140 is not in the correct location and orientation, the computer software will not be able to identify the identification symbol 140 until it is in the proper location and orientation. For example, the identification symbol 140 of FIG. 1 is asymmetrical with respect to the central longitudinal axis of the inner shaft 120. In particular, the identification symbol 140 is disposed in only part of the circumference of the inner shaft 120. Further, a longitudinal line can be seen at the "bottom" of the parallel lines 145 of the identification symbol 140 of FIG. 1. Thus, the computer software can only read the identification symbol 140 if the identification symbol is properly oriented. In the example of FIG. 1, if the catheter 100 is rotated 180 degrees such that the identification is on the far side of the catheter 100, the identification symbol 140 will appear under fluoroscopy substantially the same as in FIG. 1, except that the longitudinal line at the bottom of FIG. 1 will appear at the top of the parallel lines 145 (vertical in FIG. 1). The clinician knows that the catheter 100 is not oriented properly, and the computer program can be programmed to not read the identification symbol 140. Similarly, if the catheter is rotated approximately 90 degrees in either direction from FIG. 1, portions of the parallel lines 145 (which are circumferential) will be in the "front" of the catheter 100 and portions will be in the "back" of the catheter 100. Thus, these circumferential lines will overlap and appear shorter, and the computer software will be unable to read the identification symbol 140 properly. Other asymmetric identification symbols 140 may also be used.

Figure 9:
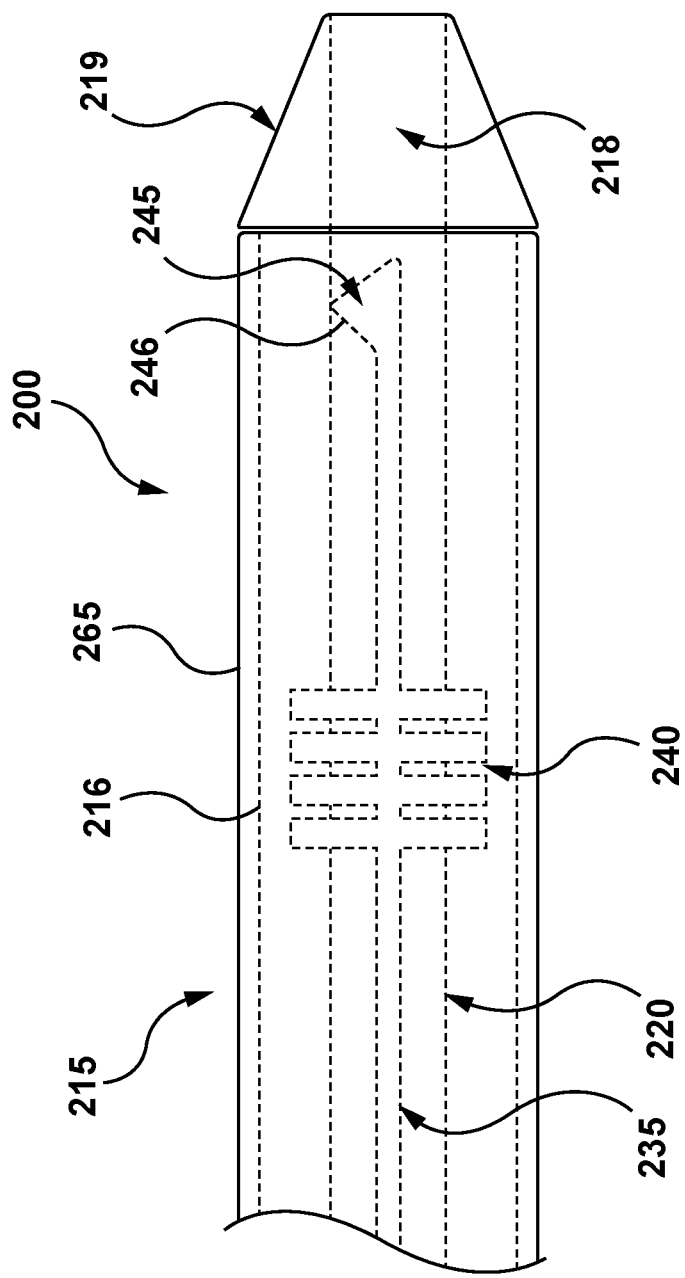
FIG. 9 is a schematic side view of a distal portion of a catheter according to another embodiment hereof.

In other embodiments, the identification symbol 140 may be symmetrical with respect to a central longitudinal axis of the catheter 100 such that the identification symbol 140 can be read in any rotational orientation (e.g. FIGS. 7-8 described above). Such an embodiment may be desirable when the rotational orientation of the catheter 100 is not critical. In other embodiments, it may be desirable to read the identification symbol in any rotational orientation, but include an additional asymmetric symbol such that the clinician may determine whether the catheter is in the proper rotational orientation. For example, and not by way of limitation, FIG. 9 shows a side view of a catheter 200 according to another embodiment hereof. In the embodiment of FIG. 9, the catheter 200 includes an outer shaft 215, an inner shaft 220 including a guidewire lumen 218, and a distal tip 219 coupled to the inner shaft 220. The catheter 200 is the type generally used with a self-expanding device that is disposed between an inner surface of the outer shaft 215 and an outer surface of the inner shaft 220. In the embodiment shown, a lumen 235 is disposed longitudinally through a wall of the outer shaft 215. As described above, the lumen 235 may be formed of a channel formed in an outer surface of a first shaft 216, and a polymeric covering 265 heat shrunk over the first shaft 216 to enclose the channel, as described in FIGS. 2A-2E but as applied to the outer shaft 215. The lumen 235 may form an identification symbol 240 as described above. In the embodiment of FIG. 9, the lumen 235 further forms a rotational identifier 245. Although the rotational identifier 245 is shown at a distal end of the lumen 235, the rotational identifier 245 can be located anywhere along the lumen either proximal or distal of the identification symbol 240. The rotational identifier 245 is asymmetric with respect to a central longitudinal axis of the catheter 200. In the embodiment shown, the rotational identifier 245 is in the form of an arrowhead. However, the rotational identifier 245 may be any asymmetric shape that allows the clinician to determine the proper rotational orientation.

Thus, when at the desired site in the vasculature, if the rotational identifier 245 is oriented in a pre-determined manner, the catheter 200 is properly oriented. For example, if the predetermined orientation is such that a tip 246 of the rotational identifier 245 is pointed upward, then the clinician can determine that the catheter 200 is properly oriented when it displays as in FIG. 9. If the tip 246 points downward, the catheter 200 is oriented incorrectly by 180 degrees. If the catheter is oriented incorrectly by some other amount, the rotational identifier 245 will not be centered in view. Also, the tip 246 points the clinician to the proper way to rotate the catheter 200 to properly orient the catheter 200. The rotational identifier 245 may also be located longitudinally to properly locate the catheter 200. For example, and not by way of limitation, the tip 246 of the rotational identifier 245 may be longitudinally located to align with a longitudinal end of a device disposed within the catheter 200. Thus, the clinician can determine when the catheter 100 is located in the proper longitudinal location prior to deployment. In other embodiments, only the rotational identifier 245 is provided, and the identification symbol 240 is not utilized.

Although specific patterns for the identification symbol have been described, other patterns are also contemplated. In addition to machine-readable patterns, patterns that form images, words, conventional symbols, letters, numbers, logos, or the like may also be utilized.

Furthermore, although the description above has been with respect to a balloon catheter having an inner shaft, it is not so limited. Thus, the lumen formed into an identification symbol may be provided on the outer shaft instead of the inner shaft, or catheters with a single shaft, or other medical devices (not limited to catheters) utilized within the body during a procedure.

While various embodiments of the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. Furthermore, there is no intention to be bound by any expressed or implied theory presented in the preceding technical field, background, brief-summary, or the detailed description. All patents and publications discussed herein are incorporated by reference herein in their entirety.

What is claimed is:
1. A catheter, comprising:
a catheter shaft including a shaft wall; and
a lumen extending longitudinally within the shaft wall, wherein the lumen is bounded in radially outward and radially inward directions, the lumen including a feed portion and an identification symbol fluidly connected to the feed portion, wherein the lumen is configured to receive a contrast media such that when filled with the contrast media, the identification symbol is machine readable.

2. The catheter of claim 1, wherein the catheter shaft includes a first shaft having an outer surface and a covering disposed around the outer surface of the first shaft, wherein the lumen comprises a channel in the outer surface of the first shaft and the covering covering the channel.

3. The catheter of claim 2, wherein the covering is a polymer film heat shrunk around the first shaft.

4. The catheter of claim 2, wherein the identification symbol comprises a series of linearly interconnected channels having varied widths.

5. The catheter of claim 2, wherein the identification symbol comprises a pattern of ablated and unablated segments of the outer surface of the first shaft.

6. The catheter of claim 5, wherein the pattern is spiral pattern wrapped around the first shaft, wherein the spiral pattern is configured to be viewed as a barcode in two dimensions using fluoroscopy when the lumen of the identification symbol is filled with contrast media.

7. The catheter of claim 6, wherein the lumen varies in width to create the identification symbol.

8. The catheter of claim 6, wherein the identification symbol is symmetrical with respect to a central longitudinal axis of the catheter shaft such that when the identification symbol is filled with the contrast media, the identification symbol is configured to be machine readable with the catheter shaft in any rotational orientation about the central longitudinal axis.

9. The catheter of claim 1, wherein the lumen comprises an air evacuation port.

10. The catheter of claim 9, further comprising an air channel extending from the air evacuation port proximally through the shaft wall of the catheter shaft, wherein the air channel and air evacuation port are fluidly connected.

11. The catheter of claim 1, wherein the identification symbol is configured such that when filled with the contrast media, the identification symbol is configured to be machine readable only when in a predetermined rotational orientation relative to a central longitudinal axis of the catheter.

12. The catheter of claim 1, wherein the identification symbol is asymmetric with respect to a central longitudinal axis of the catheter such that when filled with the contrast media the identification symbol is configured to show a predetermined proper rotational orientation of the catheter relative to the central longitudinal axis.

* * * * *